United States Patent
Park et al.

(10) Patent No.: US 7,132,431 B2
(45) Date of Patent: Nov. 7, 2006

(54) ANTI-MALARIAL COMPOUNDS

(75) Inventors: Brian Kevin Park, Liverpool (GB); Paul Michael O'Neill, Liverpool (GB); Stephen Andrew Ward, Liverpool (GB); Paul Anthony Stocks, Liverpool (GB)

(73) Assignee: The University of Liverpool (GB)

( * ) Notice: Subject to any disclaimer, the term of this patent is extended or adjusted under 35 U.S.C. 154(b) by 0 days.

(21) Appl. No.: 10/471,452

(22) PCT Filed: Mar. 14, 2002

(86) PCT No.: PCT/GB02/01410

§ 371 (c)(1), (2), (4) Date: Mar. 16, 2004

(87) PCT Pub. No.: WO02/072554

PCT Pub. Date: Sep. 19, 2002

(65) Prior Publication Data

US 2004/0152729 A1 Aug. 5, 2004

(30) Foreign Application Priority Data

Mar. 14, 2001 (GB) ............................................. 0106251
Feb. 16, 2002 (GB) ............................................. 0203735

(51) Int. Cl.
C07D 215/18 (2006.01)
A61K 31/47 (2006.01)

(52) U.S. Cl. ...................................... 514/313; 546/159
(58) Field of Classification Search ................. 546/159; 514/313
See application file for complete search history.

(56) References Cited

FOREIGN PATENT DOCUMENTS

| GB | 974348 | 1/1961 |
|---|---|---|
| WO | WO 86/06718 | 11/1986 |
| WO | WO 00/50404 | 8/2000 |

OTHER PUBLICATIONS

Werbel et al. (1986) "Synthesis, Antimalarial Activity, and Quantitative Structure–Activity Relationships of Tebuquine and a Series of Related 5–[(7–Chloro–4–quinolinyl) amino]–3–[(alkylamino)methyl][1,1'–biphenyl]–2–ols and N –Oxides" J. Med. Chem. vol. 29: 924–939.

Chemical Abstracts 120:217227, see compounds having Registry Nos. 154179–32–5 and 154179–31–4.

Chemical Abstracts 62:5557g, see compound having Registry No. 1643–45–4.

Aminoalkylphenols as Antimalarials. II. (Heterocyclic–amino)–α–amino–o–cresols. The Synthesis of Camoquin (Apr., 1948). Database Crossfire Beilstein "Online" —Beilstein Institut zur Forderung der Chemischen Wissenschaften, Frankfurt am Main, DE; Database Accession No. 300964—XP002203839.

*Primary Examiner*—Zinna Northington Davis
(74) *Attorney, Agent, or Firm*—Waddy & Patterson, P.C.; Emily A. Shouse

(57) ABSTRACT

The present invention relates to pharmaceutical compounds for use in the treatment or porphylaxis of malaria having the general formula: where: R is selected from the group consisting of dimethylamino, diethylamino, di-N-propylamino, diisopropylamino, di-N-butylamino, di-sec-butylamino, piperidinyl, piperizinyl, ethylamino, tert-butylamino; and X is selected from the group consisting of chloro, fluoro, iodo, bromo, trifluoromethyl, methoxy and methyl.

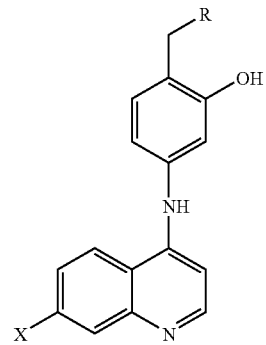

5 Claims, 6 Drawing Sheets

ANTI-MALARIAL COMPOUNDS

The present invention relates to pharmaceutical compounds which induce an anti-malarial response, to uses thereof and to a method of synthesis thereof.

Anti-malarial compounds have been used for a number of years in the control of malaria, examples include chloroquine (the most commonly used compound), primaquine, pyrimethamine, mefloquine and quinine. Resistance to chloroquine in *Plasmodium falciparum* malaria has become a major health concern of the developing world. This resistance has prompted a re-examination of the pharmacology of alternative anti-malarials that may be effective against resistant strains in order to address the growing problem. (World Health Org. Severe and Complicated Malaria W.H.O. Material Action Programme, *Trans. Roy. Trop. Med. Hyg.*, 80, 1–50). 4-aminoquinolines have the basic structure identified below:

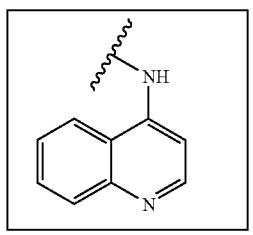

A large number of chemical entities derived from this structure are known and many have been considered as antimalarials. This art is reviewed briefly in applicant's WO-A-00/50404, which relates to 4-aminoquinolines and derivatives thereof for use in the treatment and prophylaxes of malaria WO-A-00/50404 discloses a large number of compounds which appeared from initial studies to present particularly good efficacy against chloroquine sensitive and resistant strains of *Plasmodium falciparum*.

The present inventors, in collaboration with one of the inventors name in WO-A-00/50404, have published certain work in connection with the use of 4-aminoquinoline Mannich base antimalarials in *J. Med. Chem.* 1999, 42, 2747–2751.

Ohtomo, Hiroshi et al disclose their work in connection with the pharmacokinetics of antimalarial Fansidar in healthy Japanese in *Chemical Abstracts*, Vol. 103, No. 17.

Srivastava, Sandhya et al disclose their work in connection with the synthesis of 7-chloro-4-substituted aminoquinolines and their in vitro ability to produce methemoglobin in canine hemolyzate in *Chemical Abstracts*, Vol. 128, No. 5.

Barlin, Gordon B. et al disclose their work in connection with the potential antimalarial activity of Mannich base derivatives of 4-[7-chloro (and 7-trifluoromethyl)quinolin-4-ylamino]phenols in *Chemical Abstracts*, Vol. 121, No. 21.

Barlin, Gordon B. et al disclose their work in connection with the potential antimalarial activity of Mannich base derivatives of 2-[7-(chloroquinolin-4-ylamino and 7-bromo (and 7-trifluoromethyl)-1,5-naphthyridin-4-ylamino]-4-chloro(or 4- or 6-t-butyl or 4 or 4-fluro)phenols and 4 (or 6)-t-butyl-2-(7-trifluoromethylquinolin-4-ylamino)phenol in *Chemical Abstracts*, Vol. 121, No. 15.

Natarajan, P. N. discloses work in connection with antimalarial activity and decomposition studies of 4-(7-chloro-4'-quinolylamino)- -phenyl- -piperidino-2-cresol in *Chemical Abstracts*, Vol. 80 No. 7.

Stephen J. Kesten et al disclose their work in connection with the synthesis and antimalarial effects of 4-[(7-chloro-4-quinolinyl)amino]-2-[(diethylamino)methyl]-6-alkylphenols and their N$^W$-oxides in *J. Med. Chem.* 1987, 30, 906–911.

Leslie M. Werbel et al disclose their work in connection with 4-aminoquinoline-1-oxide compounds, salts thereof and methods for obtaining them in U.S. Pat. No. 3,136,769 (the patent being assigned to Parke, Davis & Company).

F. Hoffmann-La Roche AG disclose certain aminoquinoline derivatives having antimalarial activity in EP-A-0656353.

Eli Lilly and Company disclose certain quinoline fungicides in EP-A-0326330.

One compound which is effective against chloroquine resistant strains of *P. falciparum*, is amodiaquine, which is a 4-aminoquinoline anti-malarial compound (Watkins, W. M.; Sixsmith, D. G.; Spencer, H. G.; Boriga, D. A.; Karjuki, D. M.; Kipingor, T.; Koech, D. K. Effectiveness of Amodiaquine as a Treatment for Chloroquin Resistant *Plasmodium Falciparum*. Lancet I, 1984, 357–359). However, its clinical use has been severely restricted due to associations with hepatotoxicity and agranulocytosis (Neftel, K. A.; Woodtly, W.; Schmid, M. Amodiaquine Induced Agranulocytosis and Liver Damage *Br. Med. J.*, 1986, 292, 721–723 and Lind, D. E.; Levi, J. A.; Vincent, P.C. Amodiaquine Induced Agranulocytosis; Toxic Effects of Amodiaquine in Bone Marrow Culture In Vitro. *Br. Med J.*, 1973, 1, 458–460).

Paracetamol (4-hydroxyacetanilide) contains a p-hydroxyanilino moiety which is believed to undergo P-450 catalysed oxidation to a chemically reactive quinoneimine. Amodiaquine also contains this functionality and might be expected to undergo enzymic oxidation to a reactive metabolite.

Recent studies by the inventors have shown that in the rat amodiaquine is excreted in bile exclusively as the 5' thio-ether conjugates (glutathione and cysteinyl) (Harrison, A. C.; Kitteringhatn, N. R.; Clarke, J. B.; Park, B. K. The Mechanism of Bioactivation and Antigen Formation of Amodiaquine int he Rat. *Biochem. Pharmac.*, 1992, 43, 1421–1430). This observation indicates that the parent drug undergoes extensive bioactivation in vivo to form amodiaquine quinoneimine (AQQI) or semi-quinoneimine (AQSQI) with subsequent conjugate addition of glutathione (Maggs, J. L.; Kitteringham, N. R.; Park, B. K. Drug Protein Conjugates-XIV. Mechanism of Formation of Protein Arylating Internediates From Amodiaquin a Myelotoxin and Hepatotoxin in Man. *Biochem Pharmac.*; 1988, 37, 303–311). Formation of one of these reactive species in vivo and subsequent binding to cellular macromolecules could affect cell function either directly or by immunological mechanisms. Indeed IgG antibodies which recognise the 5'-cysteinyl group have been detected in patients with adverse reactions to amodiaquine (Clarke, J. B.; Maggs, J. L.; Kitteringham, N. R.; Park, B. K. Detection of IgG Antibodies in Patients with Adverse Drug Reactions to Amodiaquine. *Int. Arch. Allergy Immunol.*, 1990, 1335–1342). Previous studies have shown that introduction of fluorine into the aromatic nucleus of paracetamol increases the oxidation potential of the molecule and thereby blocks the in vivo oxidation of the molecule to a cytotoxic quinoneimine (Barnard, S.; Kelly, D. F.; Storr, R. C.; Park, B. K. The Effect of Fluorine Substitution On the Hepatotoxicity and Metabolism of Paracetamol in the Mouse. *Biochem. Pharmac.*, 1993, 46, 841–849). Further studies demonstrated that, in a similar manner to paracetamol, the incorporation of fluorine atoms into the 4-hydroxyanilino side-chain of amodiaquine produces compounds with greater oxidative and metabolic stability (O'Neill, P. M.;

Harrison, A. C.; Storr, R. C.; Hawley, S. R.; Ward, S. A.; Park, B. K., "The Effect of Fluorine Substitution on the Metabolism and Antimalarial Activity of Amodiaquine" *Journal of Medicinal Chemistry*, 1994, 37, 1362–1370).

Amodiaquine is metabolised principally in humans to desethylarnodiaquine, a compound significantly less effective against chloroquine resistant strains (it has been suggested that this route of metabolism may have a role to play in the clinical failure of amodiaquine in patients infected with chloroquine resistant parasites). Indeed, amodiaquine has often been referred to as a pro-drug for N-desethyl amodiaquine.

Therefore an alternative strategy for providing suitable amodiaquine derivatives that do not form toxic metabolites would be advantageous. It would also be desirable for such derivatives to be potent against chloroquine resistant parasites in vivo, whilst being cheap to synthesise, enabling an affordable and effective pharmaceutical for both prophalaxis and treatment of malaria.

Isoquine (5'-(7-Chloro-quinolin-4-ylamino)-2'diethylaminomethyl-phenol) was originally synthesised in 1948 by Burckhalter and co-workers (*J. Am. Chem. Soc.* 1948, 70, 1363–1373).

More recently, Barlin (*Aust. J. Chem*, 1993, 46, 1685–1693) prepared in poor chemical yield a piperidinyl analogue of Isoquine which showed reasonable activity when compared to chloroquine sensitive and resistant parasites.

It is an object of the present invention to provide pharmaceutical compounds and their use, in particular those capable of acting in an anti-malaria manner and method of synthesis thereof.

In accordance with the first aspect of the present invention, there is provided a compound for use in the treatment or prophylaxis of malaria of the general formula:

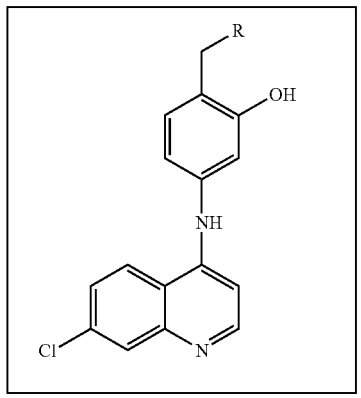

where:
R is selected from the group consisting of dimethylamino, diethylamino, di-N-propylamino, diisopropylamino, di-N-butylamino, di-sec-butylamino, piperidinyl, piperizinyl, ethylamino, and tert-butylamino; and
X is selected from the group consisting of chloro, fluoro, iodo, bromo, trifluoromethyl, methoxy and methyl.

Preferred compounds of the invention include those R is selected from the group consisting of dimethylamino, diethylamino, di-N-propylamino, diisopropylamino, di-N-butylamino, di-sec-butylamino, piperizinyl, ethylamino and tert-butylamino.

Particularly preferred compounds in accordance with the invention are those in which R is selected from the group consisting of dimethylamino, diethylamino, di-N-propylamino, diisopropylamino, di-N-butylamino, di-sec-butylamino, ethylamino and tert-butylamino. One especially preferred compound according to the invention is isoquine having the formula:

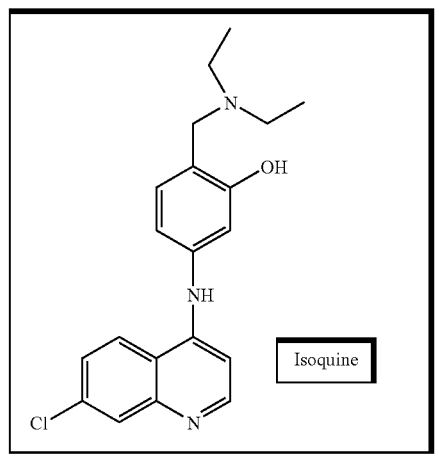

for use in the treatment or prophylaxis of malaria.

Apart from an excellent antiparasitic profile, isoquine is an extremely cheap anti-malarial to synthesise and represents a new lead for a cheap, affordable and effective anti-malarial for both prophylaxis and treatment of malaria.

Compounds according to the invention exhibit a surprisingly high level of antimalarial activity in conjunction with a reduced toxicity and effectiveness against chloroquine resistant parasites.

The invention will now be described, by way of example only, with reference to the following examples and test data.

Synthesis of 4-N-(3'-Hydroxy-4'-[N,N-diethylaminomethyl])anilino-7-chloroquinoline (Isoquine) and its Phosphate Salt.

The synthesis was conducted according to the following reaction scheme:

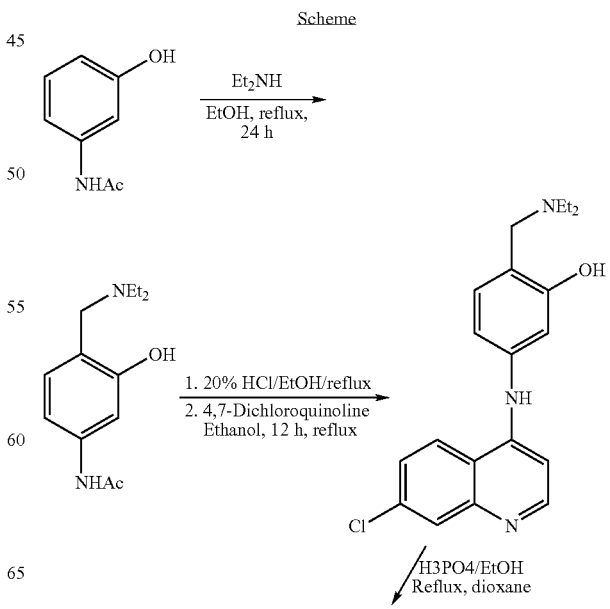

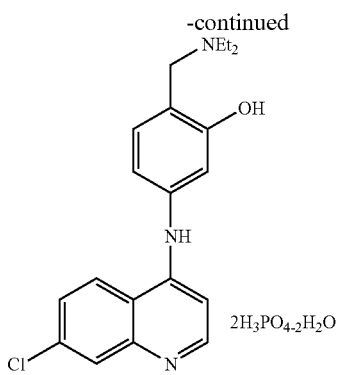

Step 1

To a round bottomed flask containing 3-acetamidophenol (5 g) in ethanol (20 ml) was added diethylamine (2.6 g) and formaldehyde (1.1 g). The resulting mixture was stirred at reflux for 24 hours. After this time, the solvent was evaporated and the residue was purified by column chromatography (silica, dichloromethane/methanol 80:20) to give N-(4-Diethylaminomethyl-3-hydroxy-phenyl)-acetamide (4.1 g, 53%). $^1$H NMR (250 MHz, CDCl$_3$) $\delta_H$: 7.05 (1H, d, J=8.2), 6.89 (1H, d, J=8.2), 6.80 (1H, s), 3.70 (2H, s), 2.60 (2H, q, J=7.2), 2.12 (3H, s, NHCOCH$_3$), 1.10 (3H, t, J=7.2). IR (NEAT) CM$^{-1}$; 3500–2800 (broad-OH band), 1668, 1614, 1538, 1454, 1386, 1273, 1194, 1166, 1114, 1032, 863, 773 and 736. ACCURATE MASS: 237.16042 gmol$^{-1}$ (C$_{13}$H$_{21}$O$_2$N$_2$ requires 237.16029); ELEMENTAL ANALYSIS; C, 64.07; H, 8.62; N, 10.88; (calc values; C, 65.67; H, 8.53; N, 11.86). MS; molecular ion peak at m/z=237

Step 2

A round bottomed flask containing 3-acetamido-6-N,N-diethylaminophenol (2 g) in ethanolic HCl (6M, 30 ml) was heated at reflux for 2 hours (20% aqueous HCl is also sufficient for this hydrolysis). The solvent was removed in vacuo and the solid was dissolved in ethanol (30 ml). 4,7-dichloroquinoline was added and the mixture was stirred at reflux for 24 hours. After this time, the solvent was removed and the product was purified by column chromatography (silica, dichloromethane/methanol 80:20) to give the desired compound as a yellow solid (2.5 g, 83%). MP; 148–150° C.: $^1$H NMR (200 MHz, CDCl$_3$); $\delta_H$: 8.53 (1H, d, J=5.5), 8.00 (1H, s, finer splitting observed, J=2.2), 7.82 (1H, d, J=8.78), 7.42 (1H, d, J=8.78, finer splitting observed, J=2.2), 7.03 (1H, d, J=5.48), 6.96 (1H, d, J=7.7), 6.72 (1H, s, finer splitting, J=1.92), 6.67 (1H, d, J=7.68, additional fine splitting, J=2.2), 3.77 (2Hs, s), 2.64 (4Hs, q, J=7.14), 1.12 (6Hs, t, J=7.14). IR (Nujol mull) cm$^{-1}$; 2930, 2858, 1668, 1612, 1575, 1529, 1459, 1424, 1378, 1327, 1277, 1192, 1178, 1159, 1115, 1079, 992, 974, 907, 873, 855, 814 and 772. MS ACCURATE MASS; 356.15169 g mol$^{-1}$ (C$_{20}$H$_{23}$ClN$_3$O requires 356.15292).

Step 3

As an alternative to the final part of step 2 above, to improve the water solubility of the final product, the diphosphate salt was prepared using a literature procedure. To the free base in ethanol at reflux was added phosphoric acid in dioxane/ethanol. The phosphate salt precipitated from the solution, was filtered and dried.

Biological Activity

In Vitro Testing Protocol

Antimalarial activity. Two strains of *P. falciparum* were used in this study: (a) The K1 strain which is known to be CQ resistant and (b) the HB3 strain which is sensitive to all antimalarials. Parasites were maintained in continuous culture using the method of Jensen and Trager. (*J. Parasitol.*, 1977, 63, 883–886) Cultures were grown in flasks containing human erythrocytes (2–5%) with parasitemia in the range of 1% to 10% suspended in RPMI 1640 medium supplemented with 25 mM HEPES and 32 mM NaHCO$_3$, and 10% human serum (complete medium). Cultures were gassed with a mixture of 3% O$_2$, 4% CO$_2$ and 93% N$_2$. Antimalarial activity was assessed with an adaption of the 48-h sensitivity assay of Desjardins et al. (*Antimicrob. Agents. Chemother.*, 1979, 16, 710–718.) using [$^3$H]-hypoxanthine incorporation as an assessment of parasite growth. Stock drug solutions were prepared in 100% dimethylsulphoxide (DMSO) and diluted to the appropriate concentration using complete medium. Assays were performed in sterile 96-well microtitre plates, each plate contained 200_l of parasite culture (2% parasitemia, 0.5% haematocrit) with or without 10_l drug dilutions. Each drug was tested in triplicate and parasite growth compared to control wells (which consituted 100% parasite growth). After 24-h incubation at 37° C., 0.5_Ci hypoxanthine was added to each well. Cultures were incubated for a further 24 h before they were harvested onto filter-mats, dried for 1 h at 55° C. and counted using a Wallac 1450 Microbeta Trilux Liquid scintillation and luminescence counter. IC$_{50}$ values were calculated by interpolation of the probit transformation of the log dose—response curve.

In Vivo Testing Protocol

Male, random Swiss albino mice weighing 18–22 g were inoculated intraperitoneally with 10$^7$ parasitised erythrocytes with *P. yoelii* NS strain. Animals were then dosed daily via two routes (intraparential or oral) for four consecutative days beginning on the day of infection. Compounds were dissolved or suspended in the vechile solution consisting of methanol, phosphate buffered saline and DMSO (2:5:3 v/v). The parasitemia was determined on the day following the last treatment and the ED$_{50}$ (50% suppression of parasites when compared to vehicle only treated controls) calculted from a plot of log dose against parasitemia.

4-N-(3'-hydroxy-4'-[N,N-diethylaminomethyl])anilino-7-chloroquinoline (Isoquine) displays superior in vitro activity compared to amodiaquine against both the chloroquine sensitive HB3 isolate of *P. Falciparum* (IC$_{50}$ 9 nM±4 versus 18 nM±7, n=4) and the chloroquine resistant K1 isolate (IC$_{50}$ 6 nM±2 versus 25 nM±8, n=4).

In Vivo

This superior activity is translated into superior in vivo activity in the *P. yoelii* NS rodent malaria model. Oral administration in the standard 4-day test (repeated twice) resulted in an ED$_{50}$ for 4-N-(3'-hydroxy-4'-[N,N-diethylaminomethyl])anilino-7-chloroquinoline of 1.6 and 3.7 mg/kg compared to 7.9 and 7.4 mg/kg for amodiaquine. Hence, the compound of the invention has improved antimalarial activity but with no cross resistance with chloroquine.

The superior activity of the compounds of the invention allows, in use of the compounds, as pharmaceutical agents, exposure to the pharmaceutical agent to be reduced, with a consequent reduction in the potential for toxicity. It is widely recognised that drugs that cause idiosyncratic toxicity (e.g. sulphonamides, anticonvulsants) are usually given in a high mass dose. Thus, the increase in potency and decrease in dose will reduce the potential toxicity of the pharmaceutical agents of the invention.

Metabolism Studies

Methods

Investigation of Biliary and Urinary Excretion of [$^3$H] AQ and [$^3$H] ISQ After Administration to Male Wistar Rats.

Male Wistar rats (200–300 g) were anaesthetised with urethane (1.4 g/ml in 20 ml in 0.9% saline, 20 ml/kg) and there state of consciousness determined, using the cornea reflex test and the limb retraction test. The rats were carefully monitored throughout the procedure to ensure that anaesthesia was maintained.

A small incision was made in the throat and the trachea was located, via blunt dissection of the surrounding connective tissue. A 1.57 mm (I.D.) polythene tube cannula was inserted and securely fastened. The jugular vein was also cannulated with 0.58 mm (I.D.) tubing to allow iv administration of the compounds. A syringe containing saline was attached to the jugular cannula to act as a seal preventing air bubbles from entering the vein. An incision was made along the midline of the abdomen. The common bile duct was located and allowed to dilate before a 0.58 mm (I.D.) cannula was inserted. Control bile was obtained. The penis was ligated, to allow urine to be collected during the experiment.

The vehicle in which the radiolabelled compounds had been made up in was 50% dimethylsulphoxide (DMSO)—49% water—1% citric acid. DMSO replaced the saline in the jugular cannula to prevent the drug precipitating out of solution during dosing.

A 500 μl Hamilton syringe was filled with either [$^3$H]AQ or [$^3$H]ISQ (54 μmol/kg, 25 μCi/kg) and connected to the cannula. The radiolabelled compounds were infused via the jugular vein over a period of 30 mins to prevent respiratory depression caused by DMSO. Bile fractions were collected at hourly intervals for 5 h from the start of dosing, All samples were weighed and there weight recorded.

After 5 h any remaining urine was aspirated from the bladder and blood was collected via cardiac puncture with a heparinised needle into a heparinised tube. The sample was centrifuged to allow the plasma and red blood cells to be separated (4000 rpm for 5 min.) The volume of plasma was recorded. Tissues (brain, heart, kidney, liver, lung, spleen and skin) were removed from the animal, rinsed in saline before being placed in vials and weighed. All samples were stored at −80° C. until they were required for analysis.

Investigation of [3H] AQ and [$^3$H] ISQ Remaining in the Plasma After Dosing.

The animal was anaesthetised and the jugular vein cannulated as described above. To allow blood samples to be taken regularly, the carotid artery was cannulated with 0.58 mm I.D. polythene tubing. The cannula was attached to a heparinised saline syringe to prevent blood escaping from the cannula and to prevent air bubbles from entering the blood stream. The animals were dosed as described above and the clock was started at the end of the dosing period. Blood samples (300 μl) were collected at 15 mins, 30 mins and hourly post-dosing. Heparinised saline was flushed through the cannula after every blood collection to prevent clotting within the tubing. The saline was allowed to drain out of the cannula prior to every collection point.

After the fifth hour sample had been collected, all remaining blood within the rat was allowed to drain from the cannula into a heparinised tube. All samples were centrifuged (4000 rpm for 5 min) immediately after collection and the pellet and supernatant were separated. The volume of the plasma was also removed and weighed all samples were stored at −80° C. until analysed. The active components of the plasma were removed via extraction with ether for LC/MS analysis.

24 Hour Metabolism Study.

[$^3$H]AQ (54 μmol/kg) was administered i.p to male Wistar rats (200–300 g). Each animal was placed in a wire-bottom metabolism cage with access to food and water. Urine was collected over 24 h, the cage was rinsed with distilled water (10 ml) at the end of the collection period. After 24 h the animals were anaesthetised with phenobarbitone (60 mg/kg in 0.9% saline), their tissues removed and blood collected via cardiac puncture with a heparinised needle. All samples were stored at −80° C. until analysed. Previous ISQ data was obtained for comparison with AQ. This data was produced following the same procedure used for AQ.

Analysis of the Radioactivity Excreted into Urine, Bile and Plasma

Aliquot of bile (2×10 μl), urine (2×50 μl) and plasma (2×50 μl) from animals dosed with [$^3$]AQ or [$^3$H]ISQ were added to 4 ml of liquid scintillant and vortexed thoroughly. Samples were left in darkness overnight to prevent chemiluminescence. Radioactivity was then determined using a Packard 1500 Liquid Scintillation Analyser.

Investigation of the Tissue Distribution of [$^3$H]AQ or [$^3$H] ISQ over 5 h.

Portions of each tissue (50–100 mg) and aliquots of red blood cells (50–60 mg) were taken in duplicate; tissue solubilizer (0.5 ml) was added to each sample and left overnight at 50° C. The samples were cooled to room temperature before being decolourised with hydrogen peroxide (200 μl) and left for 1 h. The mixture was then neutralised with glacial acetic acid (30 μl) and 12 ml of scintillation fluid was added. The mixture was mixed thoroughly and left overnight in the dark. The samples were assayed for radioactivity. (all volumes of chemicals to be added were doubled for solubulizing the red blood cells)

Analysis of Urinary, Binary and Plasma Metabolites of Male Wistar Rats Dosed with [3H]AQ or [$^3$H]ISQ.

LC/MS combines HPLC and mass spectrometry to produce a powerful analytical technique capable of identifying and separating organic compound with high molecular weights. Our samples were analysed using MassLynx software. Aliquots (50–100 μl) of bile, urine and plasma ether extracts, were eluted from a Zorbax SB-18 column with a slow acetonitrile gradient (10–50% over 30 mins) in ammonium acetate (5.0 mM, pH3.8) at 0.9 ml/min. Two Jasco PU-980 pumps were linked to a mixing module, allowing effluent to mix with scintillation fluid prior to reaching the Flo-One A250 _eta radioactive flow detector or allowing the effluent to be delivered to the Quattro II mass spectrometer. Nebulising and drying gas were delivered at a rate of 13 L/h and 300 L/h respectively. The temperature of the LC/MS interface was 70° C. and the capillary voltage was $3.7 \times 10^{-2}$ V. The extent of fragmentation was modulated via altering the cone voltage.

Materials

Opti-solv tissue solubilizer was a product of Wallac (Loughborough U.K). Ultima-gold liquid scintillation fluid was purchased from Packard bioscience. Glacial acetic acid was a merck product. [$^3$H]AQ or [$^3$H]ISQ were synthesised by the University of Liverpool. Heparin was a product of CP pharmaceuticals (Wrexham UK). All other chemicals used were purchased from Sigma (Poole, U.K.)

Statistics

All values are given as the mean±s.e.m. All statistical analyses were carried out using a Mann-Whitney test and the differences were deemed significant at $p<0.05$ The results of these investigations are reported below with reference to the accompanying drawings in which.

Figure 5:
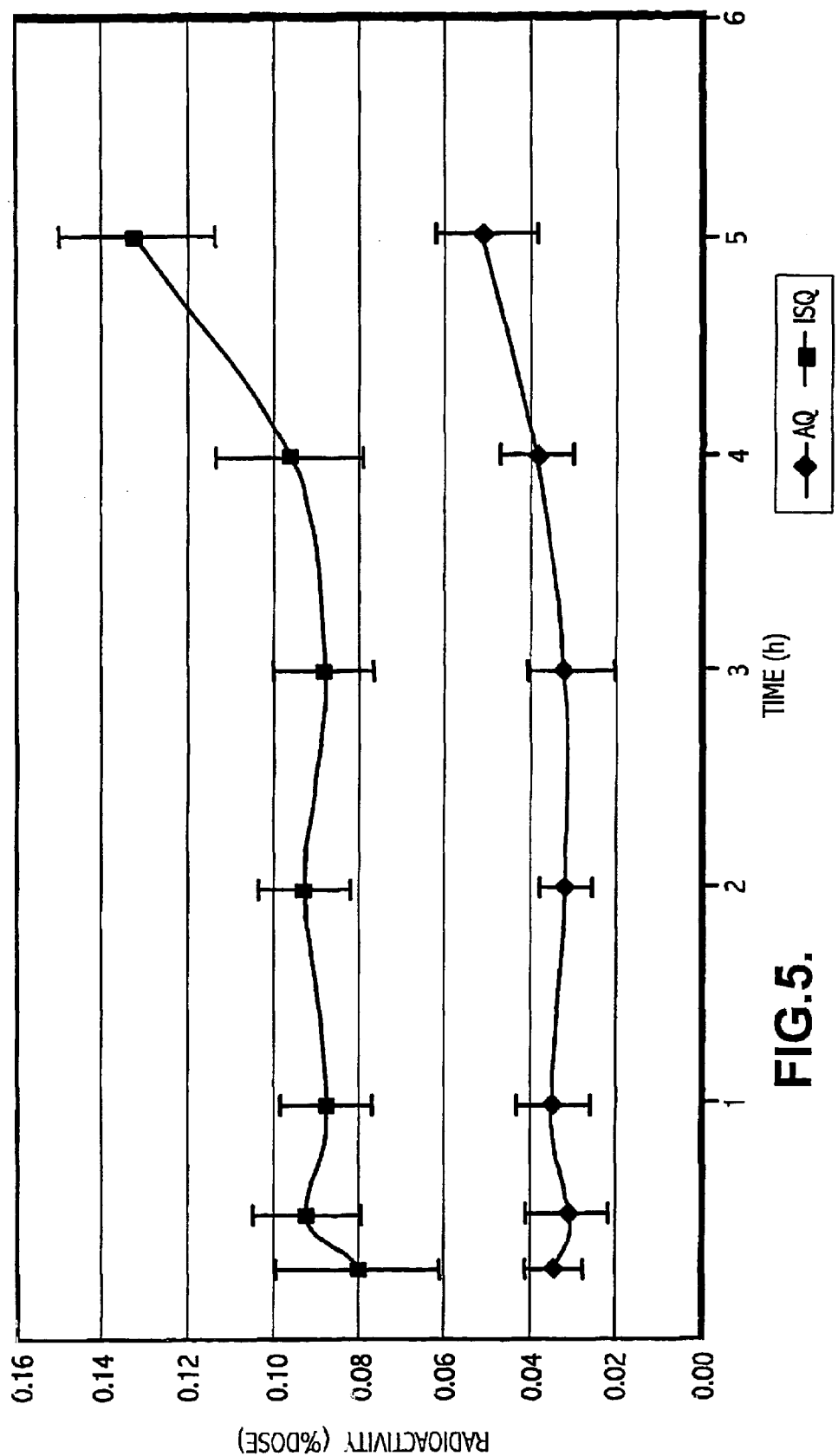

FIG. 5. shows distribution of radioactivity into plasma of rat, during the 5 h after administration of [$^3$H]amodiaquine and [$^3$H]isoquine (54 μmmol/kg, 25_uCi/kg)

Figure 6:
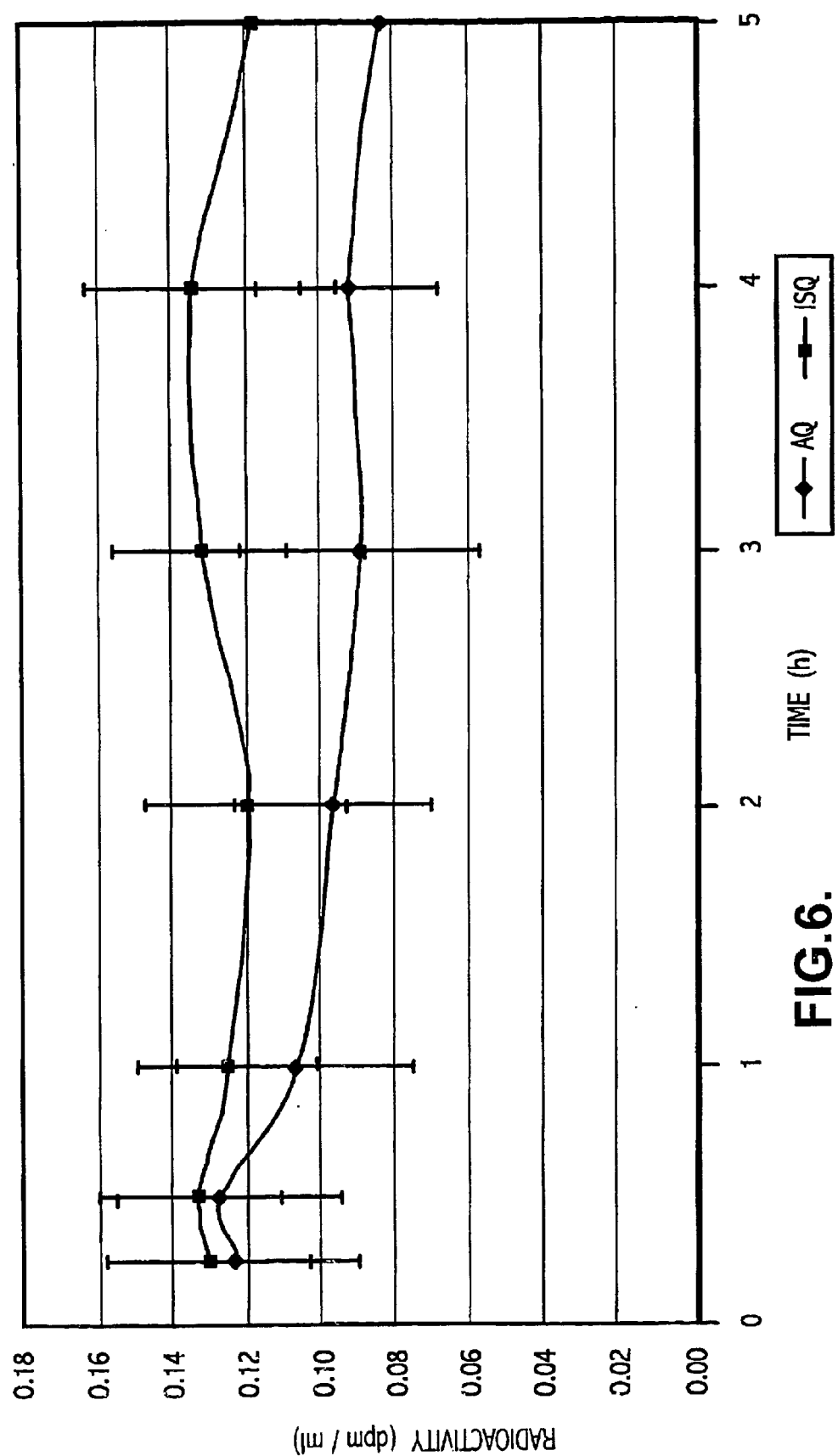

FIG. 6. shows distribution of radioactivity into red blood cells of rats, during the 5 h after the administration of [3H]amodiaquine and [$^3$H]isoquine (54 μmol/kg, 25_Cl/kg)

RESULTS

Figure 1:
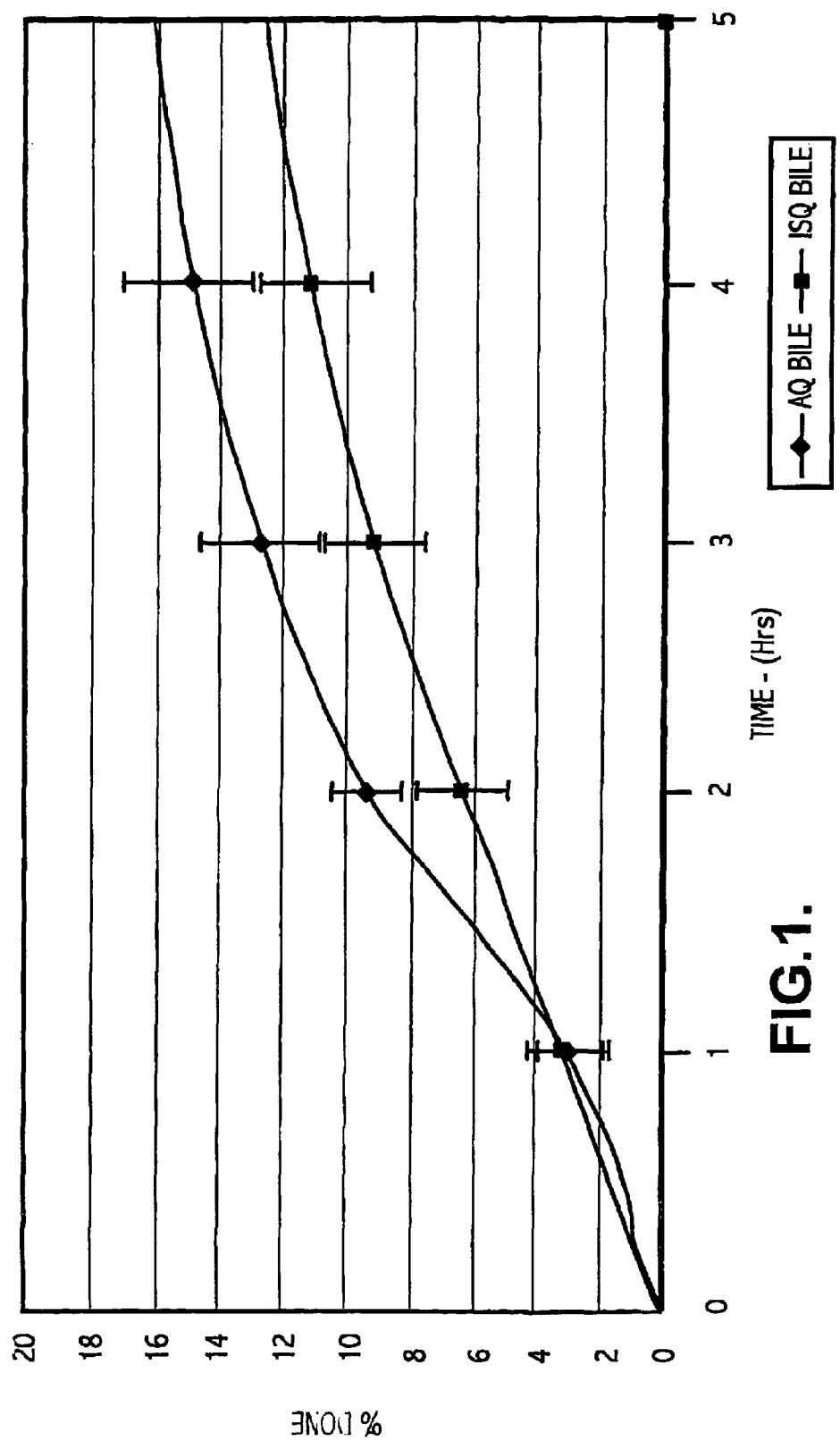
FIG. 1 shows cumulative excretion of radioactivity into rat bile, during the 5 h after administration of [3H] amodiaquine and [3H] isoquine (54 umol/kg, 25 uCi/kg.) Each point represents the cumulative % dose±s.e.m (n=4 ISQ and n=3 AQ).
Figure 2:
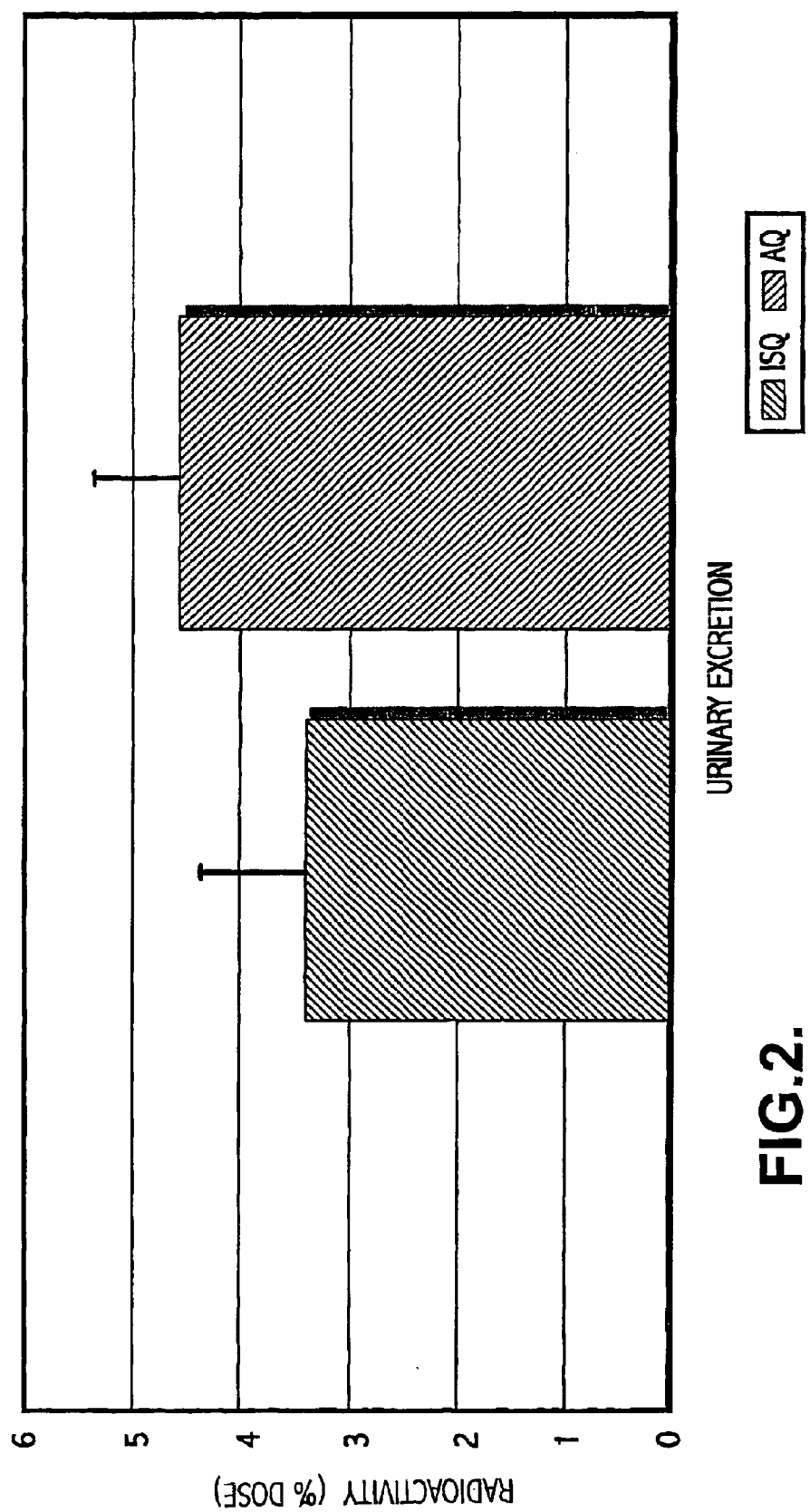
FIG. 2 shows excretion of radioactivity into urine, 5 h after the administration of [$^3$H]amodiaquine and [$^3$H] isoquine (54 μmol/kg, 25 uCi/kg). Each column represents % dose excreted±s.e.m. (n=4).

Excretion of Radioactivity After Administration of [$^3$H]AQ or [3H]ISQ to Male Rats The level of excretion of radioactivity into bile and urine following i.v administration of amodiaquine and isoquine can be seen in FIGS. 1 and 2. 5 h after the administration of AQ accounted for 16.13%±1.97% of the dose had been excreted into the bile compared to 12.73%±0.47% of the ISQ dose. The difference between these results was not shown to be significant.

The urinary excretion of AQ over 5 hrs accounted for 4.49%±0.89% dose administered to the rats. Over 5h 3.39%±1.02% of the ISQ dose was cleared by the kidneys into the urine. These results are not significantly different Tissue Distribution of Radioactivity 5 h After the Administration of [$^3$H] AQ or [$^3$H]ISQ to Male Rats.

Figure 3:
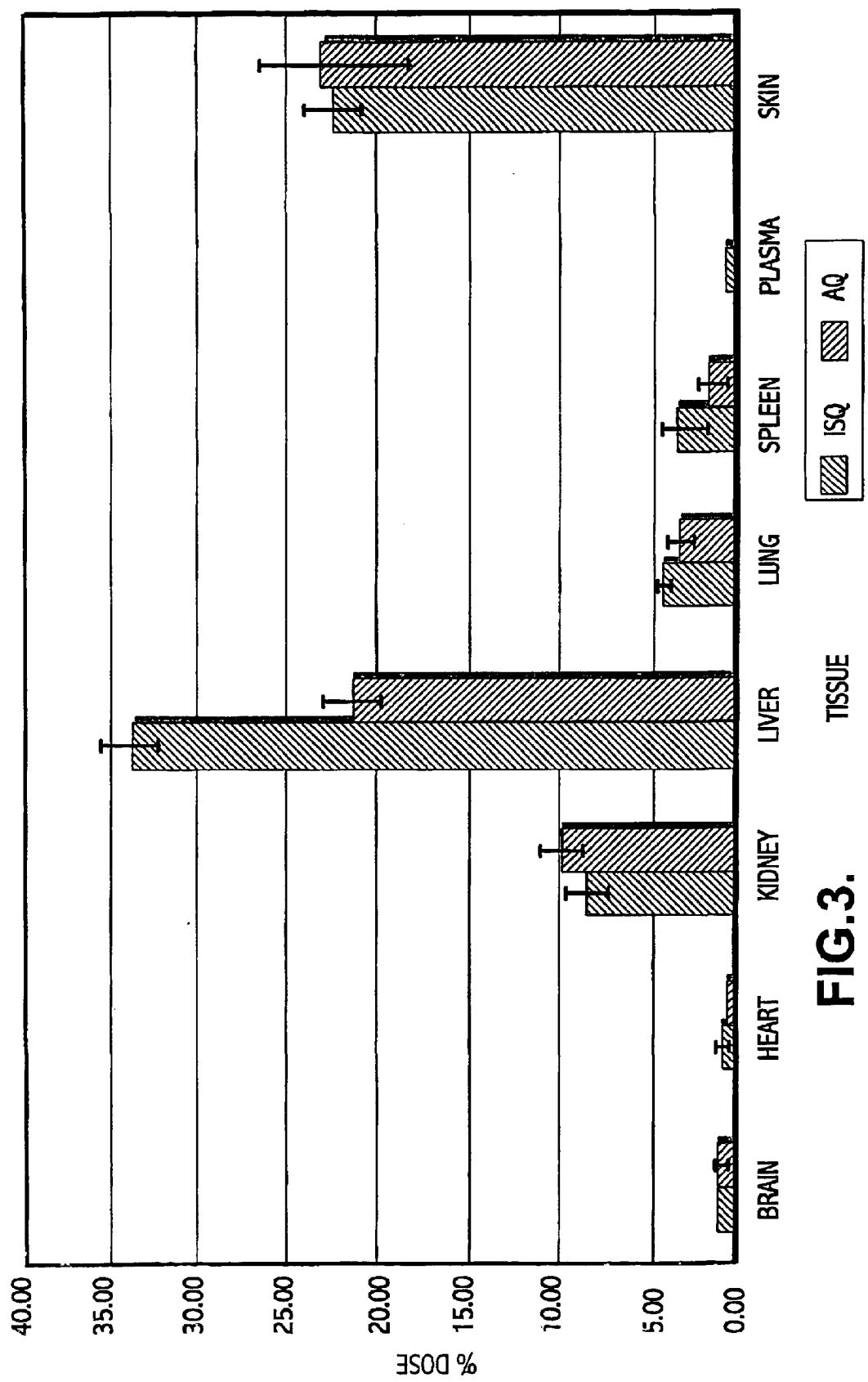
FIG. 3 shows distribution of radioactivity (shown as % of dose) in the rat, 5 h after administration of [$^3$H]amodiaquine and [$^3$H]isoquine (54 μmol/kg, 25_Ci/kg.)(n=4)

The distribution of radioactivity in the rat 5 h after the administration of either [$^3$H]AQ or [$^3$H]ISQ can be seen in FIG. 3. All of the results are expressed as a percentage of the 32.93%±2.95% of the dose remaining in this organ after 5 h. Similarly 20.82%±2.08% of the dose remained in the livers of the rats dosed with [$^3$H]AQ. This result was not deemed significant despite an approximately 10% increase in liver accumulation seen with ISQ after 5 h.

The skin was also a major site of accumulation of radiolabelled compound with 21.46%±1.89% and 22.12%±4.73% of the dose being recovered for ISQ and AQ respectively after 5 h.

Significant differences were seen with the accumulation of the radiolabelled compounds in the heart and plasma. (p=<0.05). The percentage of the dose remaining in the heart, 5 h after the administration of ISQ or AQ, was 0.58%±0.01% and 0.34%±0.04% respectively. The percentage of the dose remaining in the plasma after 5 h, accounted for 0.13%±0.03% for ISQ and 0.04%±0.01% for AQ. Plasma sample taken after 5h are deemed statistically significant however plasma sample taken during the experiment were not statistically significant.

After 5 h 87.17% of the dose could be accounted for in bile(12.73%), tissues (70.92%), plasma (0.13%) and urine (3.39%) following the administration of [$^3$H]ISQ and 78.56% of the dose could be accounted for following the administration of [$^3$H] AQ.(Bile 16.13%, tissues 57.91%, plasma 0.04% and urine 4.49%)

Tissue Distribution of Radioactivity 5 h After the Administration of [$^3$H]AQ or [$^3$H]ISQ to Male Rats.

Figure 4:
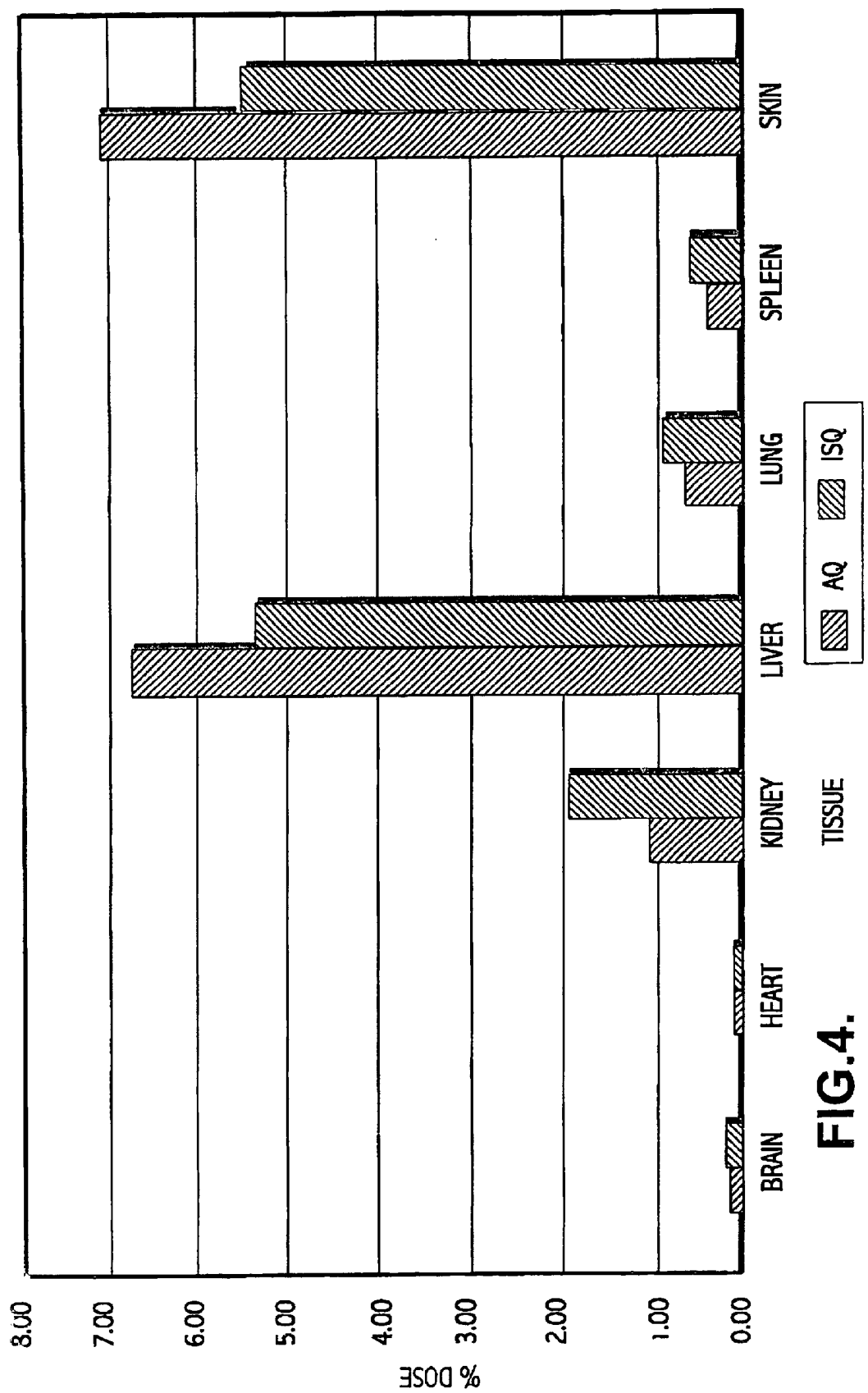
FIG. 4 shows ditribution of radioactivity (shown as % of dose) in the rat, 24 h after administration of [$^3$H] amodiaquine and [$^3$H]isoquine (54 μmol/kg, 25_Ci/kg.)

The distribution of radioactivity in the rat 24 h after the administration of either [$^3$H]AQ or [$^3$H]ISQ can be seen in FIG. 4. All of the results are expressed as a percentage of the dose for the whole organ. After 24 h only 16.15% of the dose remained in the tissue of animals given [$^3$]AQ similarly only 13.87% of the dose remained in the tissues of the animals dosed with [$^3$H]ISQ. With only 6.85% of the AQ dose remaining in the liver illustrating the loss of 13.97% of the dose being removed from this organ. 5.48% of the ISQ dose remaining in the liver after 24 h suggesting the removal and possible excretion of 27.45% of the dose.

Urine and plasma data is missing for ISQ however 8.48% of the AQ dose was recovered in urine and only 0.02% of the dose remained in the plasma. 7.18% of AQ dose remained in the skin after 24 h, the remaining tissues account for 2.12% of the dose. 5.6% of ISQ dose remained in the skin of ISQ dosed rats with the remaining tissues accounting for 2.97% of the dose.

Radioactivity Distributed in Plasma and Red Blood Cells During the 5 h After the Administration of [$^3$H]AQ and [$^3$H]ISQ.

Plasma levels remain fairly constant over the duration of the experiment (FIG. 5), with approximately 0.034% of the AQ dose remaining in the plasma throughout the duration of the experiment. The plasma levels for ISQ were 3 fold greater than those witnessed with AQ with the average plasma level being maintained at 0.095% of the dose. However this was not shown to be significant after statistical analysis.

The levels of AQ radioactivity found to be remaining in the red blood cells declined slowly over the 5 h period with a small decrease in the radioactivity recovered within the plasma (FIG. 6). Initially 0.12% of the dose remained in the plasma with only 0.09% of the dose remaining in the plasma after 5 h. The level of radioactivity remaining in the red blood cells of ISQ dosed rats, appears to have remained at a constant 0.12% throughout the experiment.

Biliary Metabolites of AQ In Vivo

After i.v administration of [$^3$H] AQ to male Wistar rats analysis of the radiochromatogran representing biliary metabolites revealed 2 peaks which were not completely resolved whilst analysing the bile from rats dosed with AQ. LC/MS analysis of these peaks revealed a glutathione conjugate of AQ (Rt=11.93 min) which gave a protonated molecule peak [M+1]$^+$ with m/z 663/661 representing the presence of a chlorine atom and also a peak [m+1−HN(Et)$_2$]$^+$m/z 588 representing the loss of the mannich side chain the glutathione conjugate.

Urinary Metabolites of AQ In Vivo

Radiochromatography performed on the urine samples collected from the rats dosed with AQ revealed 4 peaks. Analysis of the ion current chromatograms and the electrospray data suggests that the main compound excreted within the urine was unchanged AQ which produced a molecular ion peak at m/z 356 μM+1]$^+$ seen together with the fragment m/z 283 representing the loss of the diethylamino side chain. Rt=18.13 min.)

A [M+1]$^+$ peak at m/z 517 represented the AQ mercapturate metabolite and the characteristic loss of the diethylamino side chain produced a fragment m/z 444. (Rt=20.85 min.) The desethylAQ metabolite was identified by [M+1]$^+$ ions at m/z 328. This metabolite was also seen with the fragment m/z 283, representing the loss of desethyl side chain (Rt=16.35 min.)

The benzoic acid metabolite of AQ produced a molecular ion at m/z 315 and the fragment m/z 297 corresponding to the loss of water from this minor metabolite. (Rt=25.3 min.)

Biliary Metabolites of ISQ In Vivo 4 biliary metabolites of ISQ have been identified using radiochromatography and LC/MS. The main biliary metabolite associated with this compound is a isoquine aldehyde glucuronide metabolite with a retention time of 21.02 min and a [M+1]+ peak at m/z 475 and the fragment m/z 299 illustrating the loss of dehyrdroglucuronic acid (DGA).

An isoquine alcohol glucuronide metabolite was detected with m/z peaks at 477 and the fragment m/z 301 corresponding to the loss of DGA (Rt=21.02 min).

A isoquine benzoic acid glucuronide, derivative was also witnessed corresponding to the peaks m/z 491 and the loss of DGA represented by the fragment m/z 315 (Rt=18.98 min.) With these metabolites it is unknown whether the glucuronide is located on the phenol or the alcohol/carboxylic acid group.

An unconjugated isoquine benzoic acid metabolite is also excreted into the bile. With a [M+1]+ peak at m/z 315 and the fragment m/z 297 indicating the loss of water from the metabolite (Rt=24.25 min.)

A desethyl isoquine glucuronide was represented by a peak at m/z 504 and fragment at m/z 459 corresponding to the loss of the desethyl side group and also a peak at m/z 283 indicating the loss of DGA (Rt=18.30 min).

Urinary Metabolites of ISQ In Vivo

The radiochromatogram revealed 5 peaks. The main peak had a retention time of 19.49 min. This corresponded to the parent compound isoquine which produced a [M+1]+ peak with a m/z 356 and the characteristic fragment m/z 283 representing the loss of the mannich side chain.

A isoquine benzoic acid metabolite was discovered with a retention time of 24.25 min this is associated with a [M+1]+ peak m/z 315 and the fragment m/z 297 indicating the loss of water. Other minor metabolite which have been suggested as possible urinary metabolites for ISQ include desethyl isoquine glucuronide which is represented by a peak at m/z 504 (Rt=14.90 min) and the fragment m/z 459 loss of desethyl side group and m/z 283 representing the loss of dehydroglucuronic acid. Isoquine glucuronide which forms a [M+1]+ peak at m/z 532 and fragment suggesting the loss of the diethylamino side chain (m/z 459) and the loss of dehydroglucuronic acid (m/z 283) (Rt=17.88 min.)

Desethylisoquine has also been identified as a metabolite with a m/z peak of 328 and a m/z283 fragment suggesting the loss of the desethyl side group from the molecule.(Rt=18.22 min.)

Plasma Metabolites

The main compound circulating in plasma was the parent compound, ISQ. The main metabolite detected for AQ was desethylAQ. Traces are not shown. The differences in metabolic profiles of Isoquine and Amodiaquine are summarised in the following two metabolic Schemes. Clearly, ISQ has a very different metabolic profile, a profile which would not be obvious or predictable to those skilled in the field. The Scheme for AQ shows clearly metabolites derived from the toxic metabolite, amodiaquine quinone imine (AQQI).

The ability of amodiaquine to produce reactive metabolites responsible for idiosyncratic adverse reactions may be a function of the 1–4,hydroxyamino arrangement in. amodiaquine, which permits the formation of metabolites that can be monitored by the formation of GSH conjugates. The arrangement of substituents in the compounds of the present invention makes this route of bioactivation impossible. Furthermore, investigations in the rat model have failed to identify any GSH conjugates in bile, urine or blood using LCMS. The metabolic pathway for the compounds of the invention involves the formation of gucuronide conjugates of the desethyl, bisdesethyl and deaminated metabolities as compared to the GSH conjugate and desethyl metabolite observed for amodiaquine. Hence, the structural modification has removed the potential for reactive metabolite formation without any loss of biological activity.

A research strategy for providing amodiaquine derivatives that do not form toxic. metabolites, by simple oxidation was used that involved interchanging the position of the hydroxyl group and the Mannich side-chain. One such amodiaquine derivative produced in this way was Isoquine, which is an arnodiaquine regioisomer. Further studies concluded that Isoquine does not form toxic metabolites and is potent against chloroquine resistant parasites in vivo. Furthermore, this compound was found to have superior in vivo activity against *P. bergheri* in the mouse model.

Activity of possible anti-malarial compounds directed towards activity in chloroquine resistant strains of malaria is not easily predicted and surprisingly, experiments showed that the presence of diethylamino Mannich side chain imparts high potency against chloroquine resistant parasites. Furthermore the experiments showed that the activity of these Isoquine and derivative compounds were more effective than amodiaquine in vivo in the mouse model with an improved oral activity in vivo against rodent strains of malaria parasites, regardless of route of administration.

In view of the metabolic activity of administered amodiaquine, studies were initiated in order to investigate the metabolic fate of isoquine. From these studies, isoquine was also found to be N-dealkylated but, in contrast to amodiaquine, the desethyl metabolite for isoquine is a substrate for glucuronidation, which is a Phase II clearance mechanism not observed with amodiquine. This information was indicated by the presence of several glucuronide metabolites (with a complete lack of glutathione metabolites in the bile of rats) after administration of radio-labeled isoquine. The observation was in direct comparison to amodiaquine in similar metabolism studies, where glutathione metabolites were observed. The main other metabolites observed with isoqiline are side-chain cleaved products, all of which have had the N-diethylamino group oxidatively removed.

Experiments also showed that the metabolic removal of the N-diethylamino side-chains in isoquine provides metabolites with reduced anti-malaria activity, thus it was the N-diethylamino side-chain that was identified as essential for in vivo activity and that the pharmacological response is related to the concentration of the parent drug in the plasma and not a metabolite. This is in direct contrast with amodiaquine, as described, where the N-desethyl metabolite mediates the in vivo anatimalarial activity.

Studies with anti-malarials containing a cyclic Mannich side-chain have indicated that compounds in this class do not undergo side-chain cleavage, as is observed in this study. Examples include amopyroquine, the 4-aminoquinoline bispyroquine and the azaacridine derivative pyronaridine.

It is apparent from these studies described herein above that the use of Isoquine and its derivatives have clear advantages over the clinically used anti-malarial amodiaquine due to its superior activity (regardless of route of administration) to amodiaquine and chloroquine in chloroquine resistant and sensitive parasites in vitro. It is also apparent that the compounds containing N-diethylamino Mannich side chains were also safer for administration as an anti-malaria compound due to a completely altered route of metabolism in mammalian models as no evidence for metabolism to chemically reactive and potentially toxic metabolites in vivo were found in the experiments conducted.

The corresponding isoquine analogues ISQ 1–5 were synthesised by the same procedure as isoquine using the appropriate amine in the first step of the sequence. All analogues were prepared as their free bases and the following table lists their analytical data.

| Analogue | Calculated CHN | Found |
|---|---|---|
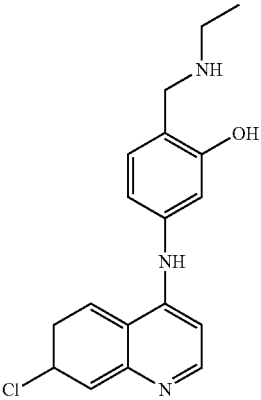
C, 65.95; H, 5.53; N, 12.82    C, 65.65; H, 5.33; N, 12.45
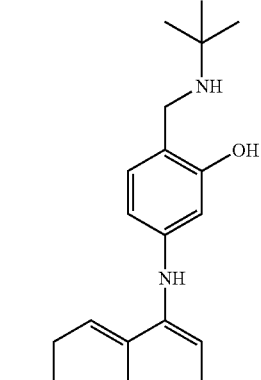
C, 67.50; H, 6.23; N, 11.81    C, 67.10; H, 6.45; N, 11.89
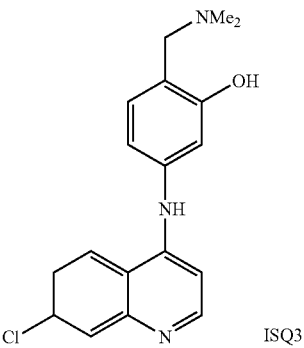
C, 65.95; H, 5.53; N, 12.82    C, 66.05; H, 5.73; N, 12.99

-continued
| Analogue | Calculated CHN | Found |
|---|---|---|
| 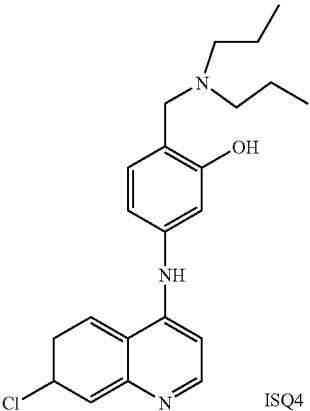 ISQ4 | C, 68.83; H, 6.83; N, 10.95 | C, 68.95; H, 6.53; N, 10.82 |
| 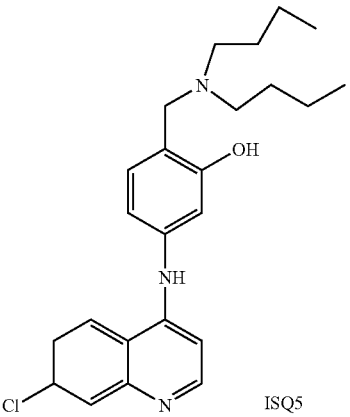 ISQ5 | C, 69.97; H, 7.34; N, 10.20 | C, 69.90; H, 7.53; N, 10.42 |
| 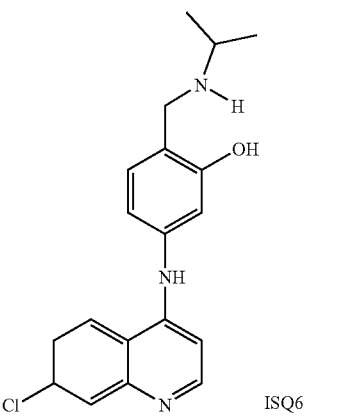 ISQ6 | C, 66.96; H, 5.90; N, 12.69 | C, 66.66; H, 5.80; N, 12.15 |

The compounds were tested against chloroquine resistant K1 *P. falciparum* and the results are shown in Table 2. All of the compounds display potent activity versus this resistant strain with IC50 values very similar to the lead compound Isoquine.

TABLE 2

In Vitro Antimalarial Activity of Isoquine and Five Analogues ISQ1–5 Versus Chloroquine Resistant K1 *Plasmodium falciparum*

| Compound | IC50 nM |
|---|---|
| Isoquine | 15.71 |
| ISQ1 | 16.47 |
| ISQ2 | 25.17 |
| ISQ3 | 23.77 |
| ISQ4 | 14.90 |
| ISQ5 | 22.74 |
| Chloroquine | Ca 190–250 |

What is claimed is:

1. A method for the treatment or prophylaxis of malaria comprising:
    administering, as an active ingredient, an effective dosage of a compound of the formula:

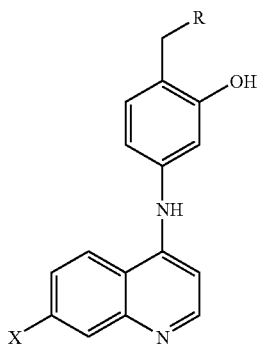
(I)

where:
   R is dimethylamino or diethylamino; and
      X is selected from the group consisting of chloro, fluoro, iodo, bromo, trifluoromethyl, methoxy and methyl.

2. A method for the treatment or prophylaxis of malaria comprising:
    administering an effective dosage of the compound
(I)

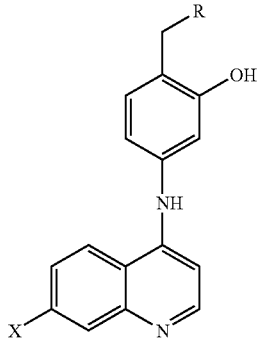

where:
   or a pharmaceutically active salt thereof, where:
   R, is dimethylamino or diethylamino; and
      X is selected from the group consisting of chloro, fluoro, iodo, bromo, trifluoromethyl, methoxy and methyl.

3. A method for the treatment or prophylaxis of chlorophine resistant strains of malaria comprising:
    administering an effective dosage of the compound
(I)

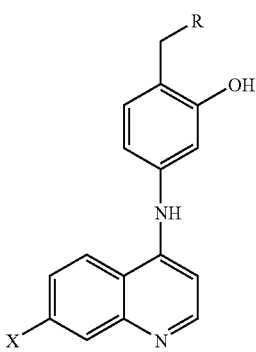

or a pharmaceutically active salt thereof, where:
   R is dimethylamino or diethylamino; and
      X is selected from the group consisting of chloro, fluoro, iodo, bromo, trifluoromethyl, methoxy and methyl.

4. A method for the treatment or prophylaxis of malaria comprising:
    administering an effective dosage of a non-toxic metabolite of the general formula:
(I)

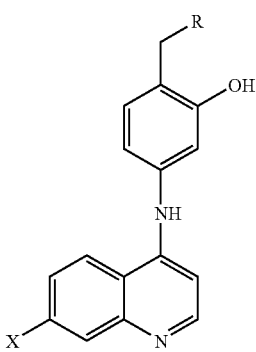

or a pharmaceutically active salt thereof, where:
   R is dimethylamino or diethylamino; and
      X is selected from the group consisting of chloro, fluoro, iodo, bromo, trifluoromethyl, methoxy and methyl.

5. A method for the treatment or prophylaxis of of chloroquine resistant strains of malaria comprising:
    administering an effective dosage of a non-toxic metabolite of the general formula:
(I)

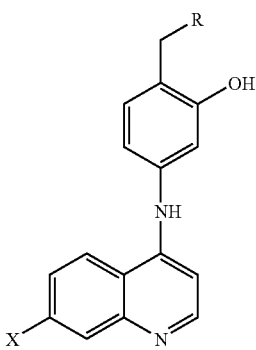

or a pharmaceutically active salt thereof, where:
   R is dimethylamino or diethylamino; and
      X is selected from the group consisting of chloro, fluoro, iodo, bromo, trifluoromethyl, methoxy and methyl.

* * * * *